US012629422B2

(12) United States Patent
Spielberg et al.

(10) Patent No.: US 12,629,422 B2
(45) Date of Patent: \*May 19, 2026

(54) AGAVE SYRUP FORMULATION OR SUSPENSION FOR ACTIVE PHARMACEUTICAL AGENTS

(71) Applicant: Genexa Inc., Atlanta, GA (US)

(72) Inventors: Max Spielberg, Miami, FL (US); David Johnson, Atlanta, GA (US)

(73) Assignee: GENEXA INC., Atlanta, GA (US)

( * ) Notice: Subject to any disclaimer, the term of this patent is extended or adjusted under 35 U.S.C. 154(b) by 287 days.

This patent is subject to a terminal disclaimer.

(21) Appl. No.: 18/636,379

(22) Filed: Apr. 16, 2024

(65) Prior Publication Data

US 2024/0258060 A1 Aug. 1, 2024

Related U.S. Application Data

(63) Continuation of application No. 17/821,138, filed on Aug. 19, 2022, now abandoned, which is a continuation of application No. 17/817,637, filed on Aug. 4, 2022, now Pat. No. 11,617,795, which is a continuation of application No. 17/342,414, filed on Jun. 8, 2021, now abandoned, which is a continuation-in-part of application No. 16/827,529, filed on Mar. 23, 2020, now abandoned, which is a continuation of application No. 15/912,785, filed on Mar. 6, 2018, now Pat. No. 10,596,266.

(60) Provisional application No. 62/580,648, filed on Nov. 2, 2017.

(51) Int. Cl.

| | |
|---|---|
| A61K 47/46 | (2006.01) |
| A61K 9/00 | (2006.01) |
| A61K 31/167 | (2006.01) |
| A61K 35/644 | (2015.01) |
| A61K 36/074 | (2006.01) |
| A61K 36/235 | (2006.01) |
| A61K 36/35 | (2006.01) |
| A61K 36/736 | (2006.01) |
| A61K 36/88 | (2006.01) |
| A61K 36/9066 | (2006.01) |
| A61K 36/9068 | (2006.01) |
| A61K 47/12 | (2006.01) |
| A61K 47/26 | (2006.01) |
| A61P 11/14 | (2006.01) |
| B23K 1/00 | (2006.01) |
| B23K 3/08 | (2006.01) |
| B23K 101/36 | (2006.01) |
| H01J 9/18 | (2006.01) |
| H01J 35/08 | (2006.01) |

(52) U.S. Cl.
CPC ............ *A61K 47/46* (2013.01); *A61K 9/0053* (2013.01); *A61K 9/0095* (2013.01); *A61K 31/167* (2013.01); *A61K 35/644* (2013.01);
*A61K 36/074* (2013.01); *A61K 36/235* (2013.01); *A61K 36/35* (2013.01); *A61K 36/736* (2013.01); *A61K 36/88* (2013.01); *A61K 36/9066* (2013.01); *A61K 36/9068* (2013.01); *A61K 47/12* (2013.01); *A61K 47/26* (2013.01); *A61P 11/14* (2018.01); *B23K 1/0016* (2013.01); *B23K 3/087* (2013.01); *H01J 9/18* (2013.01); *H01J 35/08* (2013.01); *B23K 2101/36* (2018.08); *H01J 2235/084* (2013.01)

(58) Field of Classification Search
None
See application file for complete search history.

(56) References Cited

U.S. PATENT DOCUMENTS

| | | | |
|---|---|---|---|
| 4,684,666 A | 8/1987 | Haas | |
| 5,272,137 A | 12/1993 | Blase et al. | |
| 5,560,913 A | 10/1996 | Kupper | |
| 7,101,572 B2 | 9/2006 | Santos et al. | |
| 9,801,400 B2 | 10/2017 | Cummins et al. | |
| 10,238,640 B2 | 3/2019 | Dickerson et al. | |
| 11,617,795 B2 | 4/2023 | Spielberg et al. | |
| 11,931,413 B2 | 3/2024 | Spielberg et al. | |
| 2005/0266031 A1 | 12/2005 | Dickerson et al. | |
| 2009/0148580 A1 | 6/2009 | Heyer et al. | |
| 2012/0115958 A1* | 5/2012 | Mariotti ................... | A61K 9/08 514/777 |

(Continued)

FOREIGN PATENT DOCUMENTS

| | | |
|---|---|---|
| FR | 2993457 A1 | 1/2014 |
| FR | 2993458 A1 | 1/2014 |

(Continued)

OTHER PUBLICATIONS

Paul et al.; Placebo Effect in the Treatment of Acute Cough in Infants and Toddlers A Randomized Clinical Trial; JAMA Pediatrics, 168(12):1107-1113, 2014 (Year: 2014).*

(Continued)

*Primary Examiner* — Robert A Wax
*Assistant Examiner* — John W Lippert, III
(74) *Attorney, Agent, or Firm* — MH2 Technology Law Group, LLP

(57) ABSTRACT

The present invention relates to an aqueous pharmaceutical suspension composition having from about 0.2% to 20% of a substantially water soluble pharmaceutical active, e.g. acetaminophen; a suspension stabilizing effective amount of xanthan gum and microcrystalline cellulose; an effective amount of taste masking compositions; and water, as well as a process for producing such aqueous pharmaceutical suspensions.

25 Claims, No Drawings

(56) References Cited

U.S. PATENT DOCUMENTS

| | | | |
|---|---|---|---|
| 2013/0225627 A1* | 8/2013 | Singh | A61K 31/167 |
| | | | 514/289 |
| 2013/0344217 A1 | 12/2013 | Zhang et al. | |
| 2015/0132271 A1 | 5/2015 | Chang | |
| 2016/0324207 A1 | 11/2016 | Briganti et al. | |
| 2019/0125881 A1 | 5/2019 | Spielberg et al. | |
| 2020/0338200 A1 | 10/2020 | Spielberg et al. | |
| 2021/0290532 A1 | 9/2021 | Spielberg et al. | |
| 2022/0387598 A1 | 12/2022 | Spielberg et al. | |
| 2023/0165963 A1 | 6/2023 | Spielberg et al. | |
| 2023/0321248 A1 | 10/2023 | Spielberg et al. | |
| 2024/0415971 A1 | 12/2024 | Spielberg et al. | |
| 2025/0000984 A1 | 1/2025 | Spielberg et al. | |
| 2025/0090669 A1 | 3/2025 | Spielberg et al. | |

FOREIGN PATENT DOCUMENTS

| | | |
|---|---|---|
| JP | 10167988 A | 6/1998 |
| WO | 9500133 A1 | 1/1995 |
| WO | 2012018742 A2 | 2/2012 |

OTHER PUBLICATIONS

Bhosale, R.R. et al., (2014) "Natural Gums and Mucilages: A Review on Multifaceted Excipients in Pharmaceutical Science and Research," International Journal of Pharmacognosy and Phytochemical Research, vol. 6, No. 4, 901-912.

Jani, G.K. et al., (2009) "Gums and Mucilages: Versatile Excipients for Pharmaceutical Formulations," Asian Journal of Pharmaceutical Sciences, vol. 4, No. 5, 308-322.

Tanzi, M. G. and Gabay, M. P., (2002) "Association Between Honey Consumption and Infant Botulism," Pharmacotherapy, vol. 22, No. 11, 1479-1483.

Singh, P. and Mohan, N., (2020) "Sugar and Sugar Derivatives: Changing Consumer Preferences," Springer Nat Singapore Pte Ltd. 2020, 47 pages.

Ansel, H. C. and Allen, L. V., (2014) "Pharmaceutical Dosage Forms and Drug Delivery Systems," Ansel's Pharmaceutical Dosage Forms and Drug Delivery Systems, 10th Ed.—Chapter 4, 177 pages.

Latha, R.S. and Lakshmi, P. K., (2012) "Electronic tongue: An analytical gustatory tool," Journal of Advanced Pharmaceutical Technology & Research, vol. 3, No. 1, 3-8.

Tahara, Y. and Toko, K. (2013) "Electronic Tongues—A Review," INEE Sensors Journal, vol. 13, No. 18, 3001-3011.

Pein, M. et al., (2015) "Independent comparison study of six different electronic tongues applied for pharmaceutical analysis," Journal of Pharmaceutical and Biomedical Analysis, vol. 114, 321-329.

Physicians' Desk Reference to Pharmaceutical Specialties and Biologicals, 1998 (52th Ed.)—"Children's Tylenol® acetaminophen," 5 pages.

Physicians' Desk Reference to Pharmaceutical Specialties and Biologicals, 1966 (20th Ed.)—"Tylenol® Elixir, Drops, acetaminophen," 3 pages.

McNeil Consumer Healthcare Company History of Tylenol. http://www.nancywest.net/pdfs/McNeilConsumerHealthcareCompany. pdf (Last accessed, May 18, 2023), 6 pages.

Ameer, B. and Greenblatt, D. J., "Acetaminophen," Annals of Internal Medicine, vol. 87, 202-209(1977).

Kumar, R.S. and Yagnesh, T. N. S., "Pharmaceutical Suspensions: Patient Compliance Oral Dosage Forms," World Journal of Pharmacy and Pharmaceutical Sciences, vol. 5, No. 12, 1471-1537 (2016).

Manrique, Y.J. et al., "Oral medication delivery in impaired swallowing: thickening liquid medications for safe swallowing alters dissolution characteristics," Drug Development and Industrial Pharmacy, vol. 42, No. 9 (2016), 9 pages.

Crowley, Michael M., "Solutions, Emulsions, Suspensions, and Extracts," Chapter 39 of Remington, The Science and Practice of Pharmacy, 21st Edition, pp. 745-775 (2005).

Declaration of Michael Crowley in PGR2023-00051 (Sep. 25, 2023), 242 pages.

Final Written Decision in PGR2023-00051 (Mar. 24, 2025), 47 pages.

Record of Oral Hearing in PGR2023-00051 (Jan. 28, 2025), 71 pages.

Patent Owner's Surreply in PGR2023-00051 (Oct. 11, 2024), 35 pages.

Petitioner's Reply to Patent Owner's Response in PGR2023-00051 (Sep. 6, 2024), 37 pages.

Patent Owner's Response to Petition in PGR2023-00051 (Jun. 14, 2024), 80 pages.

Decision Granting Institution of Post-Grant Review in PGR2023-00051 (Mar. 25, 2024), 27 pages.

Patent Owner's Preliminary Response in PGR2023-00051 (Jan. 3, 2024), 25 pages.

Petition for Post-Grant Review of U.S. Pat. No. 11,617,795 in PGR2023-00051 (Sep. 25, 2023), 89 pages.

FRC, "A Survey to Determine Pediatricians' Preference Between Genexa Kids' Pain & Fever and Children's Tylenol Pain + Fever Oral Suspension for Their Own 2-11 Year Old Children's Pain or Fever, Based Solely on Their Ingredients", May 24, 2021 (31 pages).

FRC, "A Survey to Determine Which One Ingredient Profile Pediatricians Prefer for Their Patients' Pain and Fever," Aug. 13, 2025 (24 pages).

FRC, "A Survey To Determine Which One Ingredient Profile Pediatricians Prefer for Their Patients' Pain and Fever," Jun. 27, 2025 (24 pages).

Office Action dated Sep. 10, 2025, in prosecution of U.S. Appl. No. 18/608,901 (20 pages).

PETA. Is Sugar Vegan ?. (Year: Jul. 2016) (7 pages).

U.S. Appl. No. 19/198,952 (13 pages).

Non-Final Office Action dated Sep. 30, 2025 in prosecution of U.S. Appl. No. 19/198,952 (21 pages).

Final Office Action dated Feb. 19, 2026 in prosecution of U.S. Appl. No. 19/198,952 (21 pages).

Response to Non-Final Action dated Dec. 30, 2025 in U.S. Appl. No. 19/198,952 (36 pages).

Non-Final Office Action dated Sep. 29, 2025 in prosecution of U.S. Appl. No. 19/198,978 (24 pages).

Final Office Action dated Feb. 25, 2026 in prosecution of U.S. Appl. No. 19/198,978 (23 pages).

Response to Non-Final Action dated Dec. 29, 2025 in U.S. Appl. No. 19/198,978 (36 pages).

Non-Final Office Action dated Feb. 26, 2026 in prosecution of U.S. Appl. No. 18/201,375 (24 pages).

U.S. Appl. No. 19/198,978 (20 pages).

Patent Owner's Demonstratives for Oral Argument in PGR2023-00051, Dec. 12, 2024, 105 pages.

D. Reker et al., "'Inactive' ingredients in oral medications," Sci. Transl. Med., 11:483 (2019), 6 pages.

J.F. Swindells et al., "Viscosities of Sucrose Solutions at Various Temperatures: Tables of Recalculated Values," Supplement to National Bureau of Standards Circular, 440 (1958), 8 pages.

P. Subramaniam and N. Nandan, "Cariogenic Potential of Pediatric Liquid Medicaments—An in vitro Study," J. Clinical Pediatric Dentistry, 36:4, 357-362 (2012).

L. Hernandez-Ramos et al., "Nutritional value and antioxidant activity of the maguey syrup (Agave salmiana and A. mapisaga) obtained through three treatments," Not. Bot. Horti. Agrobo., 48:3, 1306-1316 (2020).

Search results for "agave syrup," Merck Index Online, available at: https://merckindex.rsc.org/search-results?q=agave+syrup, Jun. 12, 2024, 2 pages.

Search Results for "agave," Combined Index to USP 40, available at: https://www.usp.org/search?search_api_fulltext=agave, Jun. 12, 2024, 3 pages.

Combined Index to USP 40 and NF 35, vols. 1-4, filed Jun. 24, 2024 in PGR2023-00051, 71 pages.

(56)            References Cited

OTHER PUBLICATIONS

SCOGS (Select Committee on GRAS Substances) Database, FDA available at: https://www.cfsanappsexternal.fda.gov/scripts/fdcc/?set=SCOGS, printed Jun. 12, 2024, 42 pages.
E. Hill et al., "Sweetener Content of Common Pediatric Oral Liquid Medications," Am. J. Hosp. Pharm. 45:135-42 (1988).
B.I. Maldonado-Guevara et al., "Production Process Effect on Mexican Agave Syrups Quality: A Preliminary Study," J. Food Res., 7:3, pp. 50-57 (2018).
E. Mellado-Mojica and M. G. Lopez, "Identification, classification, and discrimination of agave syrups from natural sweeteners by infrared spectroscopy and HPAEC-PAD," Food Chemistry, 167, 349-357 (2015).
Sep. 2021 OTC Product News, Infants' Pain and Fever, Pharmacy Times, 87:9 (2021), available at https://www.pharmacytimes.com/view/september-2021-otc, 4 pages.
Genexa "Kids' Pain & Fever Blueberry Flavor," available at https://www.businesswire.com/news/home/20200929005330/en/, printed Jun. 13, 2024, 8 pages.
Declaration of Dr. Cory J. Berkland in Support of Patent Owner's Response to Petition in PGR2023-00051 (Jun. 14, 2024), 105 pages.
"Genexa Launches First-to-Market Clean Over-the-Counter Medicine," BusinessWire (Sep. 29, 2020), 3 pages.
Petitioner's Demonstrative for Oral Argument in PGR2023-00051, Dec. 12, 2024, 152 pages.
Screen shot of U.S. Department of Agriculture Food Data Central Search Results for "Sweetener, syrup, agave," https://fdc.nal.usda.gov/fdc-app.html#/food-details/170277/nutrients, Aug. 8, 2024, 12 pages.
Page-Vault captured screen shot of National Health Institute's DailyMed entry for "Natussa Honey Free Baby Drops." https://dailymed.nlm.nih.gov/dailymed/fda/fdaDrugXsl.cfm?setid=07cbbe02-400f-4e52-83dc2d2d1336dba3&type=display. Last accessed Aug. 12, 2024, 4 pages.
Transcript of deposition of Dr. Cory Berkland, taken on Aug. 14, 2024, in PGR2023-00051, 131 pages.
Herkenne, C. et al. (2008), "Effect of Propylene Glycol on Ibuprofen Absorption into Human Skin In Vivo," Journal of Pharmaceutical Sciences, vol. 97, No. 1, 185-197.
Sun, T. and Teja, A. S. (2004), "Density, Viscosity and Thermal Conductivity of Aqueous Solutions of Propylene Glycol, Dipropylene Glycol, and Tripropylene Glycol between 290K and 460K," J. Chem. Eng. Data, 49, 1311-1317.
Screen shot of National Health Institute's DailyMed entry for "Little Remedies Infant Essentials Kit." https://dailymed.nlm.nih.gov/dailymed/fda/fdaDrugXsl.cfm?setid=be96e634-0dae-4c0b-87b2-a000da2543d3&type=display. Last accessed on Aug. 12, 2024, 5 pages.
Page-Vault captured screen shot of U.S. Food & Drug Administration's Precision FDA webpage showing Unique Ingredient Identifier (UNII) for "Agave Tequilana Juice," https://precision.fda.gov/uniisearch/srs/unii/GVG8G0207O. Last accessed on Aug. 12, 2024, 2 pages.
Neves et al. (2010), "Are paediatric medicines risk factors for dental caries and dental erosion?," Community Dental Health, 27, 46-51.
Paul, I. M. et al., (2014), "Placebo Effect in the Treatment of Acute Cough in Infants and Toddlers," A Randomized Clinical Trial, JAMA Pediatrics 168(12): 1107-1113, 2014.
AMETEK® Brookfield, Inc., (2017) "More Solutions to Sticky Problems, A guide to getting more from your Brookfield Viscometer & Rheometer," 62 pages.
Al-Achi, et al., (2005), "Physical Characteristics of Selected Over-the-Counter Medications," International Journal of Pharmaceutical Compounding; Jan./Feb. 2005; vol. 9, No. 1; Health Research Premium Collection, 7 pages.
Temple, A.R., et al., (2017), "Comparison of the Efficacy and Safety of 2 Acetaminophen Dosing Regimens in Febrile Infants and Children: A Report on 3 Legacy Studies," J Pediatr Pharmacol Ther, vol. 22, No. 1, pp. 22-32.

Perrot, D.A., et al., (2004) "Efficacy and Safety of Acetaminophen vs Ibuprofen for Treating Children's Pain or Fever," Arch. Pediatr. Adolesc. Med., vol. 158, 521-526.
Valinoti, A.C., et al., (2016) "Are Pediatric Antibiotic Formulations Potentials Risk Factors for Dental Caries and Dental Erosion?" The Open Dentistry Journal, vol. 10, 420-430.
Sinko, P. J., (2011) "Martin's Physical Pharmacy and Pharmaceutical Sciences." Physical and Biopharmaceutical Principles in the Pharmaceutical Sciences (6th Ed.), 27 pages.
Sohi, H. et al., (2004) "Taste Masking Technologies in Oral Pharmaceuticals: Recent Developments and Approaches," Drug Development and Industry Pharmacy, vol. 30, No. 5, 429-448.
Chatterjee, P. and Alvi, M. M., (2014) "Excipients and Active Pharmaceutical Ingredients." Pediatric Formulations A Road Map, Department of Pharmaceutical Sciences , College of Pharmacy and Health Sciences, Chapter 24 (20 pages).
Starbird, R., et al., "Design of Microspheres for Drug Delivery to the Colon from Blue Agave Fructans. Part 1. Esterification of Agave Fructans," J. Biobased Materials and Bioenergy, vol. 1, No. 2, 1-7, (2007).
Vera-Guzman, A. M., Aquino-Gonzalez, L. V., & Lopez, M. G. (2011). "Rheology of Agave syrup," Paper presented at the Abstracts of Papers of the American Chemical Society, 1 page.
Soto, J.L.M., et al., (2011) "Enzymatic production of high fructose syrup from agave tequilana fructans and its physicochemical characterization," African Journal of Biotechnology, vol. 10, No. 82, 19137-19143.
Rowe, R.C., ed., Handbook of Pharmaceutical Excipients (6th Ed.), 2009, 30 pages.
Priya, K. et al., (2011) "Natural Sweeteners: A Complete Review," Journal of Pharmacy Research, vol. 4, No. 7, 2034-2039.
Barclay, A. et al., (2014) "The Ultimate Guide to Sugars & Sweeteners: Discover the Taste, Use, Nutrition, Science, and Lore of Everything from Agave Nectar to Xylitol," The Experiment, LLC New York, 19 pages.
Islam et al., "Sorbitol-based osmotic diarrhea: Possible causes and mechanism of prevention investigated in rats," World Journal of Gastroenterology, vol. 21, No. 47, pp. 7635-7641, Dec. 21, 2006.
McRorie et al., "Effects of Olestra and Sorbitol Consumption on Objective Measures of Diarrhea: Impact of Stool Viscosity on Common Gastrointestinal Symptoms," Regulatory Toxicology and Pharmacology, vol. 31, pp. 59-67, Feb. 2000.
Cunha (Editor), "Sorbitol: Side Effects, Uses, Dosage, Interactions, Warnings," RxList, https://www.rxlist.com/sorbitol/generic-drug.htmm printed May 9, 2025, 21 pages.
Stevens et al., "Abstract: Dietary Sensitivities and ADHD Symptoms: Thirty-Five of Research," Sage Journals , printed May 13, 2025.
Thomson et al., "Short-term impact of sucralose consumption on the metabolic response and gutmicrobiome of healthy adults," British Journal of Nutrition, vol. 122, pp. 856-862, Sep. 13, 2019.
Schiffman et al.,"Sucralose, a synthetic organochlorine sweetener: overview of biological issues," Journal of Toxicicology and Evironmental Heath, Part B, vol. 16, pp. 399-451, 2013.
Karstadt, "Testing Needed for Acesfulfame Potassium, an Artificial Sweetener," and Soffritti, "Acesulfame Potassium: Soffritti Responds," Environmental Health Perspectives, vol. 114, No. 9, pp. A516-A519, Sep. 2006.
Lindseth et al., Author Manuscript of "Neurobehavioral Effects of Aspartame Consumption," Research in nursing & health, vol. 37, No. 3, pp. 185-193, Author Manuscript available Sep. 27, 2017.
Azad et al., "Nonnutritive sweeteners and cardiometabolichealth: a systematic review and meta-analysis of randomized controlled trials and prospective cohort studies," CMAJ : Canadian Medical Association Journal. Vol. 189, No. 28, pp. E929-E939, Jul. 17, 2017.
Danish Ministry of the Environment, "Survey and health assesment of preservatives in toys," Survey of Chemical Substances in Consumer Products, No. 124, 138 Pages, 2014.
Dodson et al., "Formaldehyde and Formaldehyde Releasing Preservatives in Personal Care Products Used by Black Women and Latinas," Environmental Science & Technology Letters, 6 Pages, May 7, 2025.

(56)　　　　References Cited

OTHER PUBLICATIONS

Dastychová et al., "Contact hypersensitivity to selected excipients of dermatological topical preparations and cosmetics in patients with chronic eczema," Acta Dermatoven APA, vol. 17, No. 2, pp. 61-68, 2008.

Bocarsly et al., Author Manuscript of "High-fructose corn syrup causes characteristics of obesity in rats: increased body weight, body fat and triglyceride levels," Pharmacology, Biochemistry, and Behavior, vol. 97, No. 1, pp. 101-106 (2012).

Ma et al., "Ghrelin receptor regulates HFCS-induced adipose inflammation and insulin resistance," Nutrition & Diabetes, vol. 3, E99, pp. 1-9, Dec. 23, 2013.

LaFee et al., "Excessive Fructose Consumption May Cause a Leaky Gut, Leading to Fatty Liver Disease," UCS San Diego Health, 6 pages, Aug. 24, 2020.

"Is Hydroxypropyl methyl cellulose safe for humans?" Chemical Book, 2 pages, 2024.

"What Are The Hydroxypropyl Methylcellulose Side Effects," ECHEMI.com, 4 pages, Dec. 9, 2021.

Millchap et al., Abstract, "The diet factor in attention-deficit/hyperactivity disorder," Pediatrics, vol. 129, No. 2, 1 page, published online Jan. 9, 2012.

Cordeiro et al., "Allergic Contact Dermatitis after the Use of Cosmetics Containing Parabens: Systematic Review and Meta-analysis," Brazilian Archives of Bilogy and Technology, vol. 65, 10 pages, 2022.

Chatterjee et al., "Parabens as the double-edged sword: Understanding the benefits andpotential health risks," Science of the Total Environment, vol. 954, 17 pages (2024).

Engeli et al., "Interference of Paraben Compounds with Estrogen Metabolism by Inhibition of17B-Hydroxysteroid Dehydrogenases," International Journal of Moecular Sciences, vol. 18, 13 pages, published Sep. 19, 2017.

Milman, "US cosmetics are full of chemicals banned by Europe—why?" The Guardian, 6 pages, May 22, 2019.

Cherian et al., "Amended Safety Assessment of Parabens as Used in Cosmetics," Cosmetic Ingredient Review, 211 pages, Aug. 29, 2018.

European Food Safety Authority (EFSA), "Scientific Opinion on the re-evaluation of dodecyl gallate (E 312) as a food additive," EFSA Journal, vol. 13, No. 5, 39 pages, First published May 5, 2015.

Wagner, "Inert Reassessment-Propyl Gallate (CAS Reg. No. 121-79-9)," United States Environmental Protection Agency, 15 pages, Dec. 30, 2005.

Xiong et al., "Connections Between Food Additives and Pschiatric Disorders," Pschiatric Times, vol. 41, Issue 4, 10 pages, Apr. 25, 2024.

Suez et al., "Artificial sweeteners induce glucose intolerance by altering the gut microbiota," Nature, vol. 514, 17 pages, Oct. 9, 2014.

Reuber, "Carcinogenicity of Saccharin," Environmental Health Perspectives, vol. 25, pp. 173-200, Aug. 1978.

Fowler et al., "Fueling the Obesity Epidemic? Artificially Sweetened Beverage Use and Long-term Weight Gain," Obesity, vol. 16, Issue 8, pp. 1894-1900, Free Access first published Sep. 6, 2012.

* cited by examiner

AGAVE SYRUP FORMULATION OR SUSPENSION FOR ACTIVE PHARMACEUTICAL AGENTS

TECHNICAL FIELD

This application relates to aqueous suspensions and formulations. This application also relates to a pharmaceutical suspension composed of pharmaceutical active agents, suspension agents, sweetening agents and flavoring agents.

BACKGROUND

Children and older persons can have problems swallowing tablets or capsules. In these situations, it is desirable to provide drugs either in a chewable solid form or in a liquid form/syrup. It is not an uncommon practice for a parent to prefer giving the sick children, usually those below the age of 12, syrup instead of tablets. Syrups are suited for children. The dose is in volumes and often can be tailored to the child's body weight. Many syrups can be flavored, which improves intake and compliance by children.

One problem is that liquids containing analgesic, antihistamine, and diuretic active pharmaceutical agents taste terrible and pharmaceutical chemists have turned to unnatural and artificial ingredients to mask the taste. No liquid medium, primarily of natural ingredients, containing this combination of active agents are available.

Accordingly, there is a need for an improved pharmaceutical suspension or syrup formulation.

SUMMARY

One aspect includes a stable, pharmaceutical syrup formulation or suspension for oral administration having one or more pharmaceutical active agents, agave syrup, and a dilutant. The syrup formulation can have a viscosity of less than 1500 centipoise at 22 degrees.

Another aspect includes a stable, pharmaceutical syrup formulation or suspension for oral administration having a pharmaceutical active agent, agave syrup, acidic preservative, a sweetening agent, a flavoring agent, and a dilutant. The syrup formulation can have a viscosity of less than 1500 centipoise at about 22 degrees.

Another aspect includes a pharmaceutical suspension that can enhance the taste masking of unpalatable pharmaceutical active agents with generally natural ingredients. One embodiment includes the use of clean inactive ingredients that are gluten-free, non GMO, and certified vegan. Other embodiments may exclude unnatural ingredients such as aspartame, carbomer, EDTA, gelatin, milk, parabens, polyethylene glycol, titanium dioxide, and other unnatural ingredients.

Another aspect includes pharmaceutical suspensions made with the same active ingredients needed for a treatment, but without the artificial not needed.

Another aspect includes a suspension that can be used as a formulation of pharmaceutical suspension. The following pharmaceutical active agents are suitable for use with the suspension including but not limited to acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, and simethicone and suitable combinations thereof.

DETAILED DESCRIPTION

This application provides a pharmaceutical suspension or syrup formulation that can be used with various active pharmaceutical agents. In one embodiment, a pharmaceutical syrup formulation for oral administration includes one or more pharmaceutical active agents, agave syrup, and a dilutant. A pharmaceutical syrup formulation for oral administration can also include an acidic preservative, a sweetening agent, and a flavoring or masking agent. The term "agave syrup" is referred to as a processed juice obtained from the agave sp. plant (e.g. also referred to as processed sap or processed aguamiel). The term "syrup" means a formulation that has a flow without applied pressures and is sticky or tacky to the touch.

The syrup can have a viscosity of the type used with pharmaceutical suspensions or syrup formulations. The syrup can have a viscosity of between about 200 and 3500 centipoise at about 2.5 rpm to about 30 rpm as determined by a Brookfield Viscometer at about 22 degrees. Further, the syrup can have a viscosity of between about 350 and about 1500 centipoise. For example, the syrup formulation can a viscosity of about 1500 centipoise at about 22 degrees. For example, the syrup formulation has a viscosity of about 1000 centipoise at about 22 degrees. For example, the syrup formulation has a viscosity of about 600 centipoise at about 22 degrees. In many examples, the viscosity of the syrup can be less than 2000 centipoise, less than 1750 centipoise, less than 1500 centipoise, less than 1000 centipoise, less than 750 centipoise, less than 600 centipoise, or less than 500 centipoise.

In one embodiment, the pharmaceutical suspension or syrup formulation can be used to administer pharmaceutical active agents with generally natural ingredients. For example, a pharmaceutical suspension can include the use of clean inactive ingredients that are gluten-free, non-GMO, and certified vegan. Other embodiments may exclude ingredients such as aspartame, carbomer, EDTA, gelatin, milk, parabens, polyethylene glycol, titanium dioxide, and other unnatural ingredients. Certain embodiments can be designed to provide pharmaceutical suspensions made with the same active ingredients needed for a treatment, but without the artificial ingredients.

In another embodiment, a pharmaceutical suspension or syrup formulation includes between 0.01 to 4 w/w % of one or more active pharmaceutical agents, 0.01 and 1% w/w % of an acidic preservative, 0.05 to 5 w/w % of a sweetening agent or flavoring agent, 50% to 98% agave syrup, and water. In one example, the one or more active pharmaceutical agents can be one of the following active agents: dextromethorphan hydrobromide, guaifenesin, or acetaminophen.

In one embodiment, a pharmaceutical suspension includes between 0.5 to 2 w/w % of one or more active pharmaceutical agents, 65% to 98% agave syrup, and water.

In one embodiment, a pharmaceutical suspension includes between 0.5 to 2 w/w % of one or more active pharmaceutical agents, 0.5 and 2% w/w % of an acidic preservative, 1 to 3 w/w % of a sweetening agent or flavoring agent, 75% to 95% agave syrup, and water.

The amount of water or dilatant in the suspension may be reduced to optimize the formulation. The amount of the pharmaceutical active agent dissolved in the suspension can be reduced. This reduction in amount dissolved reduces the need for taste masking. Since, the pharmaceutical active agent remains in the solid (undissolved) form, the pharmaceutical is less likely to be tasted while in the mouth.

The pH of the pharmaceutical suspension or syrup formulation can range from about 4 to about 10. In certain examples, the pH of the suspension can be in the range from 4 to 8. The suspension can be buffered to maintain the pH of the suspension in the desired pH range. Suitable buffers that are not chemically reactive with the other ingredients may be present in the suspension in amounts enough to provide the desired degree of pH buffering. The buffers can range from 0.01 to 1 gram per 100 mL of the suspension. In one example, the acidic preservative can be adjusted to keep the pH of the suspension at a desired level.

In one embodiment, the pharmaceutical suspension or syrup formulation may include about 0.1 to 5 grams of a pharmaceutical active agent per 100 ml of suspension. The amount of the pharmaceutical active agent in the suspension should be enough to provide a therapeutic amount of the pharmaceutical active agent and a convenient dosage unit. Up to about 0.01 to 2 grams pharmaceutical active per 100 mL may be readily included in the suspension system. However, this may vary depending on the pharmaceutical active agent and amounts are known to those with ordinary skill in the art or are readily available or can be determined using pharmaceutical science.

The water added to the pharmaceutical suspension or syrup formulation should be kept at a minimum, to facilitate masking the bitter taste of acetaminophen. The acetaminophen suspension should contain in the range from about 0.1 to 2 grams of water per 100 ml of suspension.

The suspension can be used as a formulation of a pharmaceutical suspension. The following pharmaceutical active agents are suitable for use with the inventive suspension including but not limited to acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, and simethicone and suitable combinations thereof. In one embodiment, the pharmaceutical active agents are water soluble or hydrophilic.

Therapeutic combinations of pharmaceutical active agents can include combinations of acetaminophen, ibuprofen or famotidine with pseudoephedrine hydrochloride, chlorpheniramine maleate, astemizole, terfenadine, dextromethorphan hydrobromide, guaifenesin or diphenhydramine for formulations of cold or sinus medication. Acetaminophen, ibuprofen and famotidine could also be combined with antacids to control the gastric irritation caused by these analgesics.

In one embodiment, the pharmaceutical suspension or syrup formulation can effectively mask the bitter taste of pharmaceuticals contained in the suspension. Masking the flavor of bitter pharmaceuticals may be accomplished by using flavoring agents to overpower the bitter flavor of the pharmaceutical. The bitter flavor also can be minimized by limiting the amount of water present in the suspension. Suitable sweetening agents include but are not limited to sugars such as monosaccharides, disaccharides and polysaccharides. Examples of suitable sugars include but are not limited to xylose, ribose, glucose, mannose, fructose, dextrose, sucrose, and maltose, and sugar alcohols such as sorbitol, xylitol, mannitol, glycerin and combination thereof. Presently preferred as a sugar sweetener is fructose provided as an aqueous solution. The amount of sugar sweetener used in the suspension will vary depending on the degree of sweetening desired for the suspension. Generally, the amount of sugar sweetener will be in the range of from about 0 grams to about I gram of sugar sweetener per 100 mL of the suspension.

Flavoring agents also may be added to the pharmaceutical suspensions or syrup formulations to improve the palatability of the suspension. Examples of suitable flavoring agents include natural and artificial flavors such as mints (i.e., peppermint, etc.), menthol, cinnamon, vanilla, artificial vanilla, chocolate, artificial chocolate, both natural and artificial fruit flavors (i.e., cherry, grape, orange, strawberry, etc.) and combinations of two or more thereof. Flavoring agents are generally provided as a minor component of the suspension in amounts effective to provide a palatable flavor to the suspension. However, flavoring agents are generally present in the suspension in amounts in the range of from about O grams to about 5 grams per I 00 mL of the suspension.

Optimum masking of the taste of the pharmaceutical active agents m the pharmaceutical suspension or syrup formulation can be achieved by limiting the amount of water in the suspension. As a minimum, the amount of water present in the suspension may be limited to that amount necessary to hydrate the agave syrup. The minimum amount of water also must provide the suspension with enough aqueous base to impart the desired degree of viscosity. For example, if agave syrup is used in the suspension as a sweetener, the total amount of water contained in the suspension be in the range of about 5 to 20 grams per 100 mL of suspension. Accordingly, if a bitter or unpalatable pharmaceutical active is present in the suspension, the amount of water in all the ingredients should be kept to a mm 1 mum.

Wetting agents also may be employed in the inventive suspension to facilitate the dispersion of hydrophobic pharmaceutical active agents. The concentration of wetting agents in the suspension should be selected to achieve optimum dispersion of the pharmaceutical active within the suspension with the lowest feasible concentration of wetting agent. It should be appreciated that an excess concentration of wetting agent may cause the suspension to flocculate. Those skilled in the art are well versed in suitable empirical methods to determine the appropriate wetting agents and concentrations to achieve optimum dispersion and avoid flocculation.

Coloring agents, while not generally used and are generally not preferred, can be incorporated in the suspension to provide an appealing color to the suspension. The coloring agents should be selected to avoid chemical incompatibilities with the other ingredients in the suspension. Suitable coloring agents for use in pharmaceutical suspensions are well known to those skilled in the art.

In one embodiment, the pharmaceutical suspension or syrup formulation can be prepared by mixing one or more active agents with agave and then adding water to achieve a desired consistence. One method of making a pharmaceutical syrup formulation for oral administration can include adding an amount of agave into a vessel; warming the amount of the agave in the vessel; adding an amount of one or more pharmaceutical agents to the warmed agave in the vessel; stirring the contents of the vessel until the contents are mixed; adding diluent through the process to achieve a desired viscosity of less than, e.g., 1500 centipoise, 1000 centipoise, 600 centipoise, or 400 centipoise.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

EXAMPLES

The invention will now be illustrated by examples. The examples are not intended to be limiting of the scope of the present invention but read in conjunction with the detailed and general description above, provide further understanding of the present invention and an outline of a preferred process for preparing the compositions of the invention.

Example 1: Acetaminophen Suspension

| Ingredient | Function | Amount (w/w %) |
|---|---|---|
| Pharmaceutical Active Agent (e.g., Acetaminophen) | Treatment | 1.8 |
| Agave syrup | Base | 92 |
| Citrus acid | Preservative | 0.20 |
| Masking Agent/Blueberry | Flavoring | 0.60 |
| Water | Diluent | Remaining |

In Example 1, the citrus acid and masking agent are optional and are not needed for a suitable or usable formulation.

Example 2: Preparation of Suspension 100 mg of active agent can be added to 100 mL of agave (heated). The mixture is stirred, and water can is added to achieve a desired consistency. Other agents such as sweetening agent and flavoring agent can be added to the suspension.

The invention claimed is:

1. A pharmaceutical syrup formulation for oral administration comprising:
   (a) an active pharmaceutical agent,
   (b) agave syrup, and
   (c) a water-based diluent, wherein the syrup formulation has a viscosity of less than 1000 centipoise at about 22 degrees Celsius; wherein the active pharmaceutical agent is suspended in the syrup; wherein the syrup is palatable; and wherein, other than the active pharmaceutical agent, the pharmaceutical syrup formulation does not comprise unnatural ingredients.

2. The pharmaceutical syrup formulation of claim 1, wherein the syrup formulation has a viscosity of less than 750 centipoise at about 22 degrees Celsius.

3. The pharmaceutical syrup formulation of claim 1, wherein the syrup formulation has a viscosity of less than 600 centipoise at about 22 degrees Celsius.

4. The pharmaceutical syrup formulation of claim 1, wherein the viscosity ranges from 350 to 600 centipoise at approximately 22 degrees Celsius.

5. The pharmaceutical syrup formulation of claim 1, wherein the viscosity ranges from 250 to 350 centipoise at approximately 22 degrees Celsius.

6. The pharmaceutical syrup formulation of claim 1, wherein 0.01 to 2 grams of the active pharmaceutical agent is suspended per 100 mL of the syrup formulation.

7. The pharmaceutical syrup formulation of claim 1, wherein 0.01 to 1 gram of active pharmaceutical agent is suspended per 100 mL of the syrup formulation.

8. The pharmaceutical syrup formulation of claim 1, wherein 0.01 to 5 grams of active pharmaceutical agent is suspended per 100 mL of the syrup formulation.

9. The pharmaceutical syrup formulation of claim 1, wherein the active pharmaceutical agent is selected from the group consisting of an antitussive, antihistamines, non-sedating antihistamines, decongestants, expectorants, mucolytics, analgesics, antipyretics, anti-inflammatory agents, local anesthetics, and mixtures thereof.

10. The pharmaceutical syrup formulation of claim 1, wherein the active pharmaceutical agent is acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, or simethicone.

11. A stable pharmaceutical syrup formulation for oral administration consisting essentially of:
   (a) an active pharmaceutical agent;
   (b) agave syrup;
   (c) a preservative to extend shelf life;
   (d) a flavoring agent to enhance palatability, and
   (e) a water-based diluent, wherein the formulation is maintained with a viscosity of less than 1000 centipoise at about 22 degrees Celsius, with the active pharmaceutical agent effectively suspended in the syrup; and wherein other than the active pharmaceutical agent, the pharmaceutical syrup formulation does not comprise unnatural ingredients.

12. The pharmaceutical syrup formulation of claim 11, wherein the active pharmaceutical agent is between 0.01 to 2% of the formulation by weight.

13. The pharmaceutical syrup formulation of claim 11, wherein the diluent is about 5% of the formulation by weight.

14. The pharmaceutical syrup formulation of claim 11, wherein the agave syrup is less than 98% of the formulation by weight.

15. The pharmaceutical syrup formulation of claim 11, wherein the agave syrup is less than 95% of the formulation by weight.

16. The pharmaceutical syrup formulation of claim 11, wherein the diluent is water.

17. The pharmaceutical syrup formulation of claim 11, wherein the preservative comprises citric acid.

18. The pharmaceutical syrup formulation of claim 11, wherein the composition is a medicinal preparation formulated as a syrup; and wherein the composition has a viscosity from about 600 centipoise to about 200 centipoise at about 22 degrees Celsius.

19. The pharmaceutical syrup formulation of claim 11, wherein the formulation is orally administered for veterinary and human use.

20. The pharmaceutical syrup formulation of claim 11, wherein the active pharmaceutical active agent selected from the group consisting of dextromethorphan, guaifenesin, pseudoephedrine, acetaminophen, phenylephrine and combinations thereof.

21. A stable, palatable pharmaceutical syrup formulation for oral administration consisting of:
   (a) a therapeutically effective amount of an active pharmaceutical agent;
   (b) agave syrup;
   (b) an acidic preservative;
   (c) a flavoring agent, and
   (d) a diluent, wherein the syrup formulation has a viscosity of less than 1000 centipoise at about 22 degrees Celsius and the active pharmaceutical agent is suspended in the syrup; and
   wherein other than the active pharmaceutical agent, the pharmaceutical syrup formulation does not comprise unnatural ingredients.

22. The formulation of claim 21, wherein the agave syrup is less than 98% of the formulation by weight.

23. The formulation of claim 21, wherein the agave syrup is about 95% of the formulation by weight.

24. The pharmaceutical syrup formulation of claim 23, wherein the preservative comprises citric acid.

25. The pharmaceutical syrup formulation of claim 23, wherein the active pharmaceutical agent is acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, or simethicone.

* * * * *